(12) United States Patent
Tsai

(10) Patent No.: US 7,500,401 B2
(45) Date of Patent: Mar. 10, 2009

(54) SWIVEL JAW FACE FOR TENSILE AND SIMILAR TESTING

(75) Inventor: Kuo Tsing Tsai, Singapore (SG)

(73) Assignee: Illinois Tools Works Inc., Glenview, IL (US)

( * ) Notice: Subject to any disclaimer, the term of this patent is extended or adjusted under 35 U.S.C. 154(b) by 6 days.

(21) Appl. No.: 11/787,509

(22) Filed: Apr. 17, 2007

(65) Prior Publication Data

US 2008/0257120 A1     Oct. 23, 2008

(51) Int. Cl.
*G01N 3/02* (2006.01)
(52) U.S. Cl. ....................................................... 73/859
(58) Field of Classification Search ............ 73/855–860
See application file for complete search history.

(56) References Cited

U.S. PATENT DOCUMENTS

| | | | | |
|---|---|---|---|---|
| 4,456,293 A | * | 6/1984 | Panissidi ..................... 294/106 |
| 4,562,715 A | * | 1/1986 | Brun et al. ..................... 72/167 |
| 4,843,888 A | * | 7/1989 | Gram et al. .................... 73/856 |
| 4,850,231 A | * | 7/1989 | Ralfs et al. ..................... 73/859 |
| 5,054,324 A | * | 10/1991 | Pohl .............................. 73/859 |
| 5,060,521 A | * | 10/1991 | Cole et al. ..................... 73/857 |
| 5,567,870 A | * | 10/1996 | Harris ............................ 73/81 |
| 5,945,607 A | * | 8/1999 | Peppel et al. ................. 73/856 |
| 5,965,823 A | * | 10/1999 | Ryan et al. .................... 73/860 |
| 6,007,762 A | * | 12/1999 | Amateau et al. ............. 266/118 |
| 6,126,892 A | * | 10/2000 | Amateau et al. ............. 266/118 |
| 7,047,819 B2 | | 5/2006 | Hayford et al. |
| 7,066,033 B2 | * | 6/2006 | Tanner ......................... 73/856 |

OTHER PUBLICATIONS

U.S. Appl. No. 11/410,686, filed Apr. 24, 2006, Hayford, et al.

* cited by examiner

*Primary Examiner*—Max Noori
(74) *Attorney, Agent, or Firm*—Day Pitney LLP

(57) ABSTRACT

A wedge action grip for tensile or similar testing is provided with a pair of jaws wherein at least one jaw includes a swiveling element with a gripping surface. The jaw and associated swiveling element may have cylindrical swiveling surfaces whereby the swiveling element swivels with a single degree of freedom about a vertical or horizontal axis or may have spherical swiveling surfaces whereby the swiveling element swivels with two degrees of freedom about a point. The two jaws may have different swivel characteristics, and one of the jaws may have a non-swiveling fixed gripping surface.

20 Claims, 5 Drawing Sheets

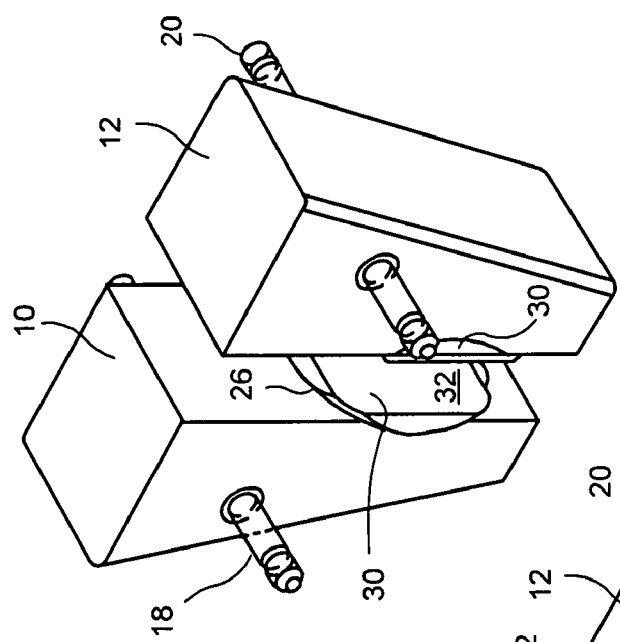
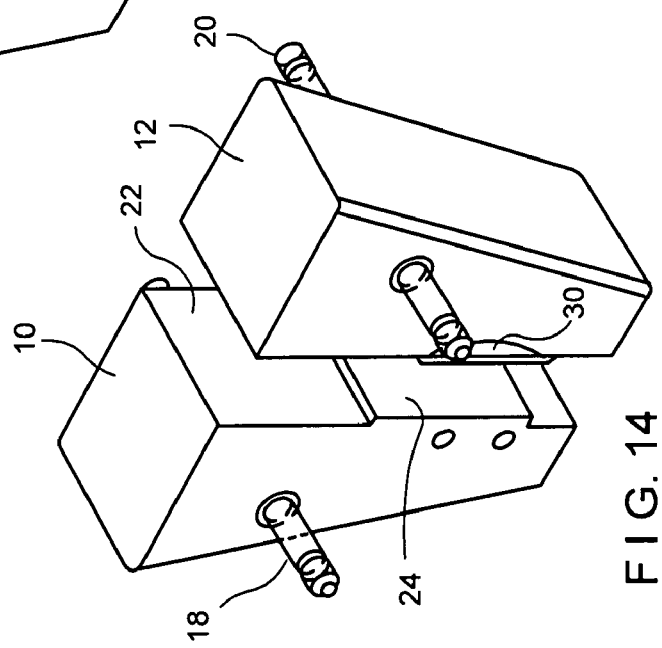
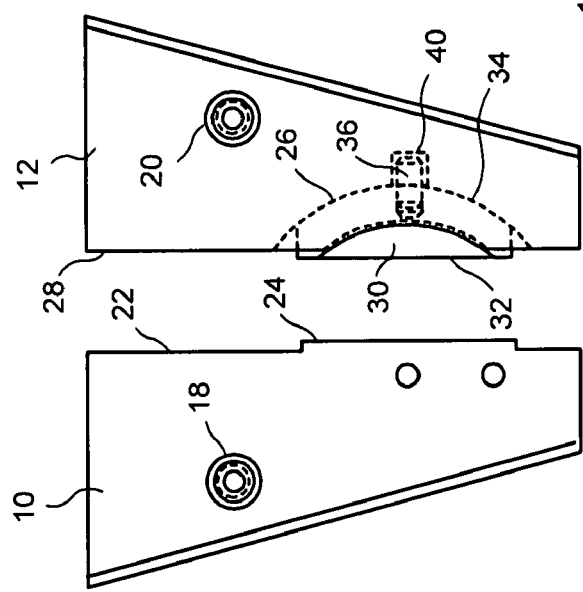
FIG. 13
FIG. 14
FIG. 12 ional patent application Ser. No. 11/410,686 entitled "Testing of

SWIVEL JAW FACE FOR TENSILE AND SIMILAR TESTING

BACKGROUND OF THE INVENTION

1. Field of the Invention

The present invention pertains to a grip for tensile and similar testing, with at least one jaw which includes a swivel face with one or two degrees of freedom in order to accommodate variations in the surface of the test specimen while maintaining a secure grip on the test specimen.

2. Description of the Prior Art

The art of tensile testing, along with similar methods of testing such as shear testing and compression testing, is well-developed. An example of a device used in such testing is a video extensometer as disclosed in U.S. Pat. No. 7,047,819 entitled "Testing of Samples", issued on May 23, 2006 and patent application Ser. No. 11/410,686 entitled "Testing of Samples", filed on Apr. 24, 2006. These devices generate stress/strain curves for a tested sample. In order to measure the strain, which is calculated through the percentage of linear deformation of the sample under testing, video targets, such as two dots, are placed on the sample. The extensometer uses video methods to determine the change in distance between the targets during testing, thereby calculating the strain. As the cross-sectional area of the target is calculated prior to testing and the force applied to the target is recorded, the resulting stress can be correlated with the strain to generate a traditional stress/strain curve.

Devices known as "wedge action grips" are commonly used to grip the samples in such testing machines. These grips utilize the taper angle of the body and jaw face to apply a parallel side acting force to grip the specimen. In most grips, a force is applied to the base of the jaw face pushing it vertically with respect to the body, so that the taper or wedge causes the jaw to close horizontally. Force can be manually applied through a screw thread, a lever arm, a gear or similar devices, or through powered means such as electric, pneumatic or hydraulic power through a piston or a motor. Typically, in all methods which move the jaw face with respect to the grip body, the surface of the jaw faces are maintained in parallel configuration to each other by the grip body. The jaw faces therefore are assumed to engage the flat, parallel faces of the test specimen. However, typically, neither the jaw faces nor the sample faces are exactly parallel. This is due to the manufacturing tolerances of the body angles and jaw faces of the grip, deflection of the grip body under stress changing the angle of the gripping surface against the specimen and the quality of the test specimen.

This lack of parallelism between jaw face and the surface of the specimen results in uneven engagement of the serration of the jaws into the specimen surface. For some materials, this is acceptable but for others, this will result in specimen slippage. The existing solution to this has been to utilize high powered grips that will exert sufficient clamping force to overcome the lack of parallelism. Similarly, in the prior art grip design, with specimens of uneven surface, the fixed face of the jaws may create bending moments causing uneven stresses on the specimen which can, under many circumstances, distort the test results.

Additionally, the prior art jaws use a gripping surface of a fixed material. That is, to change the gripping surface, the entire jaw must be changed. This adds to the complexity of operating the device. Additionally, there may be some selected circumstances, such as with a laminated or layered sample, wherein it may be desired to have opposed jaws with two different gripping surfaces to accommodate two different exposed surface materials.

OBJECTS AND SUMMARY OF THE INVENTION

It is therefore an object of the present invention to provide a jaw or grip for tensile or similar testing whereby the sample to be tested can be gripped reliably, notwithstanding variations in the surface of the sample.

It is therefore a further object of the present invention to provide a jaw or grip for tensile or similar testing wherein the gripping surface can be changed simply and further wherein the gripping surfaces of opposed jaws can be changed independently from each other.

It is therefore a still further object of the present invention to provide a jaw or grip for tensile or similar testing whereby a sample can be gripped by a method which is simple for users and whereby accurate test results are obtained.

These and other objects are attained by providing a grip with a jaw with a face which swivels, with one or two degrees of freedom, in response to the contours of the sample to be tested. This assures that the sample is gripped reliably with a minimum of user intervention, and further assures that the sample is not unduly distorted by the grip itself.

DESCRIPTION OF THE DRAWINGS

Further objects and advantages of the invention will become apparent from the following description and claims, and from the accompanying drawings, wherein:

FIG. 12 is a plan view, partially in phantom, of the jaws of the present invention, one with a swivel face which swivels about two degrees of freedom in a partially spherical seat, another with a fixed gripping surface.

FIG. 13 is a perspective view of two opposed jaws of the present invention, each with a swivel face which swivels about two degrees of freedom in a partially spherical seat.

FIG. 14 is a perspective view of the jaws of the present invention, one with a swivel face which swivels about two degrees of freedom in a partially spherical seat, another with a fixed gripping surface.

DETAILED DESCRIPTION OF THE PREFERRED EMBODIMENTS

Figure 1:
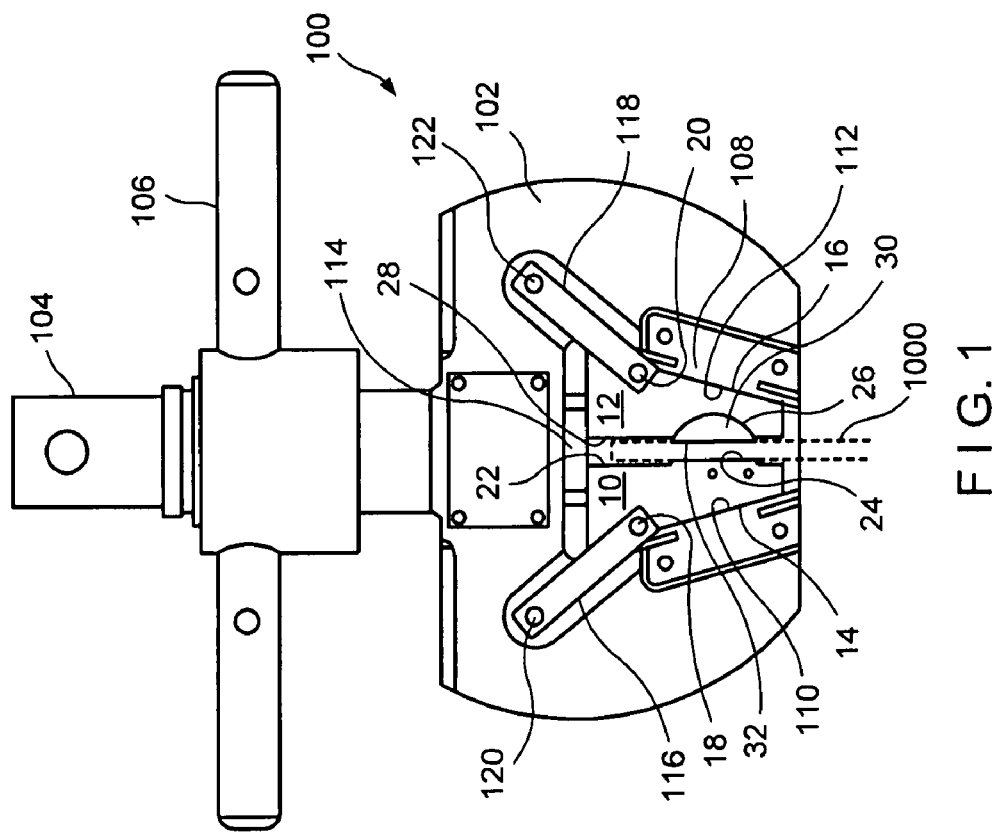
FIG. 1 is a plan view of the jaws of the present invention in a wedge action grip, with the test sample shown in phantom.
Figure 4:
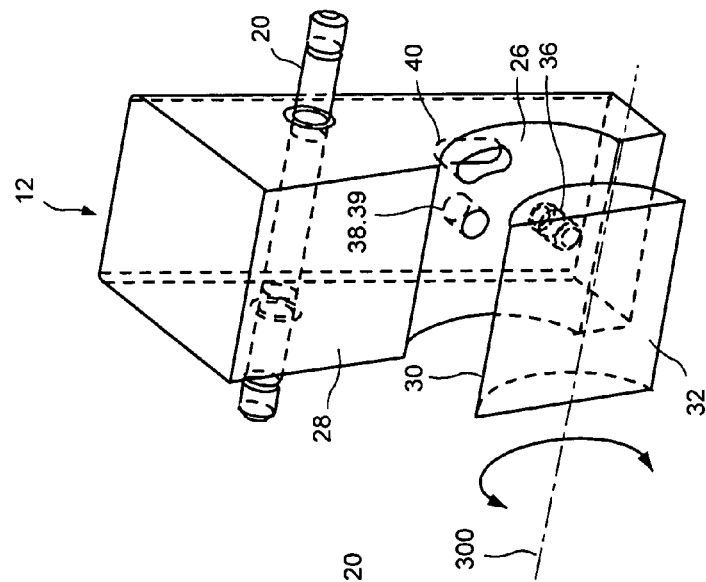
FIG. 4 is a partially exploded view of a single jaw of the present invention, shown with a swivel face which swivels with one degree of freedom about a horizontal axis.

Referring now to the drawings in detail wherein like numerals indicate like elements throughout the several views, one sees that FIG. 1 is a plan view of a wedge action grip 100 which includes head 102 affixed to a tensile/compression force bar 104 which can apply a tensile or compressive force against a sample 1000 (shown in phantom) held therein. Typically, the tensile testing apparatus (not shown) includes two heads 102 which engage opposite ends of sample 1000 and apply the testing forces to sample 1000. Head 102 includes cavity 108 for receiving opposed jaws 10, 12. Jaws 10, 12 have respective outer inclined faces 14, 16 which are seated with channels of respective inner inclined faces 110, 112 of cavity 108. Plunger 114 is used to force jaws 10, 12 in a downward direction (in the orientation shown in FIG. 1) thereby urging jaws 10, 12 toward each other thereby increasing the gripping force against sample 1000. Plunger 114 typically includes a threaded shaft (not shown) within head 102, thereby allowing a user to adjust the position of plunger 114 by turning rotary handle 106, thereby adjusting the strength of the grip on sample 1000. The first ends of coil springs 116, 118 are attached to respective posts 120, 122 on head 102 and the second ends of coil springs 116, 118 are attached to respective posts 18, 20 on jaws 10, 12. Coil springs 116, 118 provide an upward and outward (or spreading apart) motion to jaws 10, 12 in the absence of force applied by plunger 114.

Figure 2:
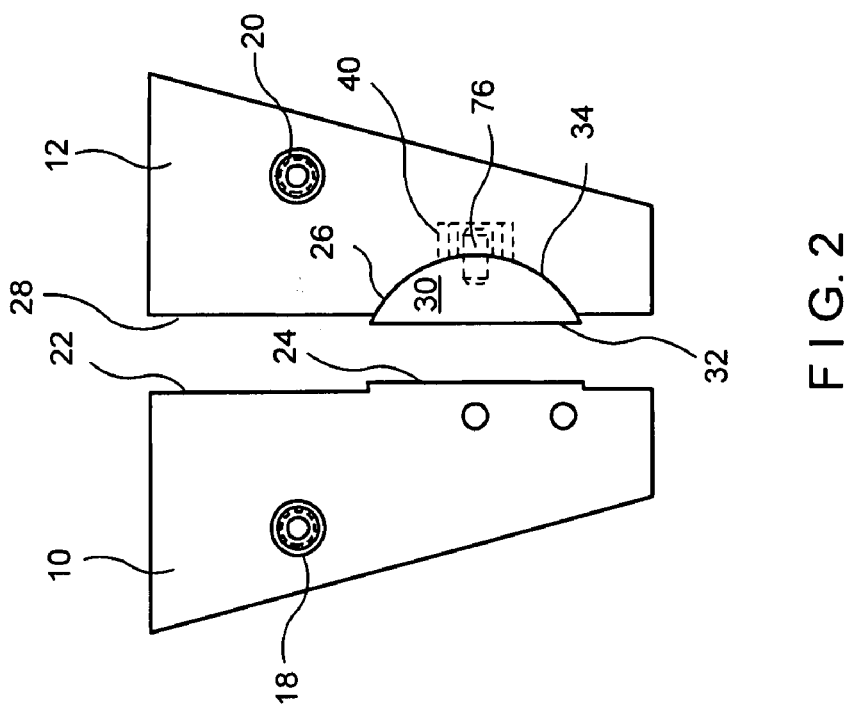
FIG. 2 is a plan view of the jaws of the present invention, shown with a single swivel face which swivels with one degree of freedom, opposing a fixed face.
Figure 3:
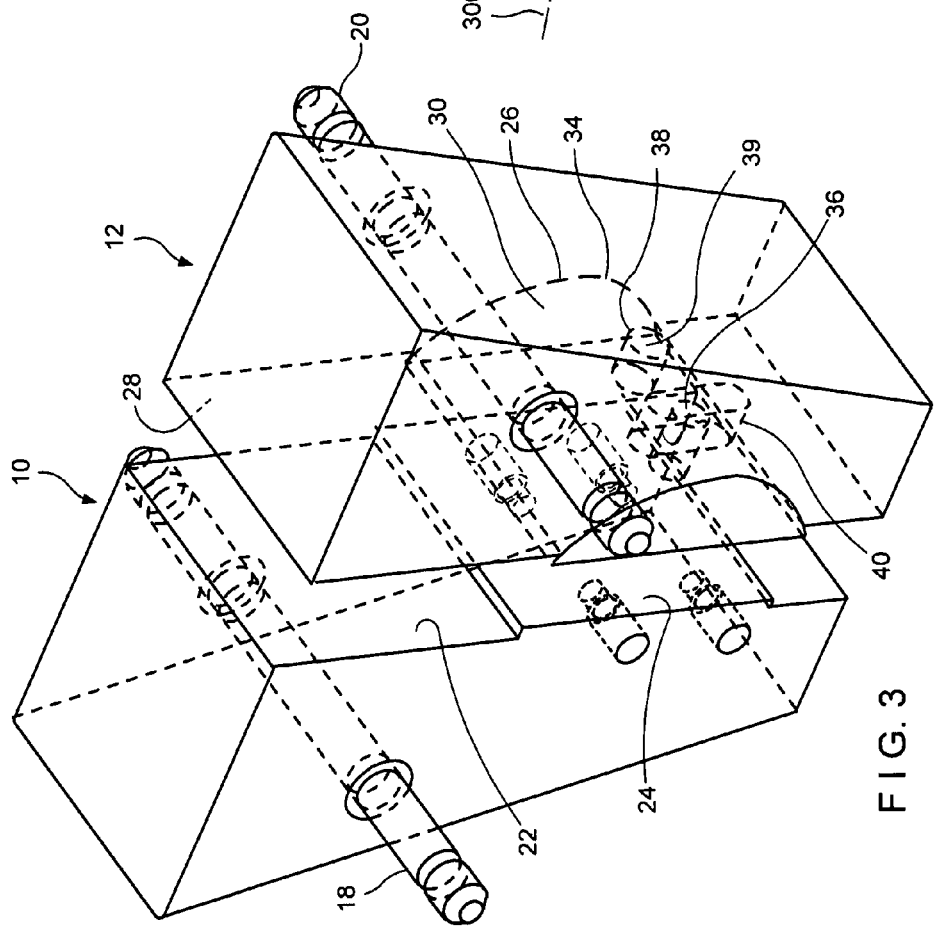
FIG. 3 is a perspective view, partially in phantom, of the jaws of the present invention, shown with a single swivel face which swivels with one degree of freedom about a horizontal axis, opposing a fixed face.

In FIGS. 1-3, jaw 10 includes inner face 22 with a slightly protruding fixed gripping face 24. Fixed gripping face 24 can be of any suitable gripping surface including, but not limited to, serrations, rubber coated, smooth ground and surf-alloy compound. In FIGS. 1-4, jaw 12 includes concave seat 26 formed in inner face 28 of jaw 12 in the shape of a portion of a cylinder with a horizontal axis 300 (all discussions of axes being "horizontal" or "vertical" are with respect to the illustrated orientations with downwardly pointing jaws). Swivel element 30 includes a generally flat gripping face 32, typically formed with one of the gripping surfaces listed for fixed gripping face 24 and further includes a rear convex face 34 which is a portion of a cylinder with a horizontal axis, formed so as to be complementary with concave seat 26, thereby allowing swivel element 30 to seat and rotate about the common horizontal axis with a single degree of freedom, with flat gripping face 32 slightly protruding from inner face 28. The capture of the swivel element 30 within concave seat 26 may be achieved in several ways, such as a dove-tail structure, a retaining screw or a permanent magnet. In FIG. 2, pin 36 protrudes from rear convex face 34 of swivel element 30, extending into slot 40 formed in concave seat 26. The dimensions of slot 40 can be used to limit the range of rotation or swiveling of swivel element 30. Additionally, cylindrical blind aperture 38 is formed in the concave seat 26 of jaw 12 and permanent magnet 39 is placed therein to attract swivel element 30 to remain in concave seat 26.

Figure 5:
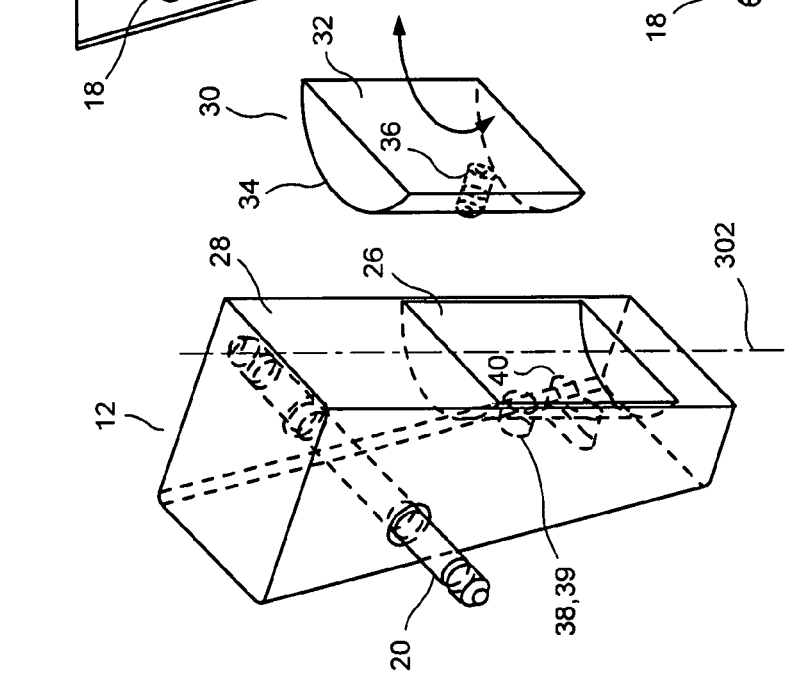
FIG. 5 is a partially exploded view of a single jaw of the present invention, shown with a swivel face which swivels with one degree of freedom about a vertical axis.

FIG. 5 shows a configuration wherein the common cylindrical axis of concave seat 26 and rear convex face 34 is vertical, thereby permitting swiveling of swivel element 30 about vertical axis 302.

Figure 6:
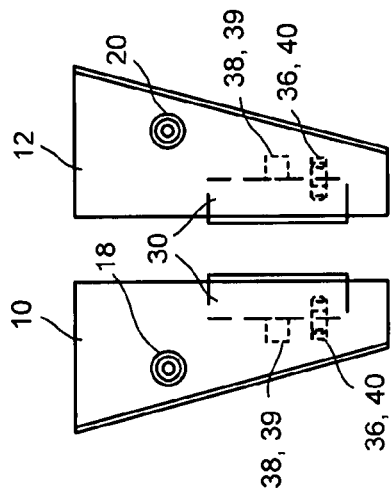
FIG. 6 is a plan view, partially in phantom, of the jaws of the present invention, one with a swivel face which swivels with one degree of freedom about a vertical axis, another with a fixed gripping surface.
Figure 8:
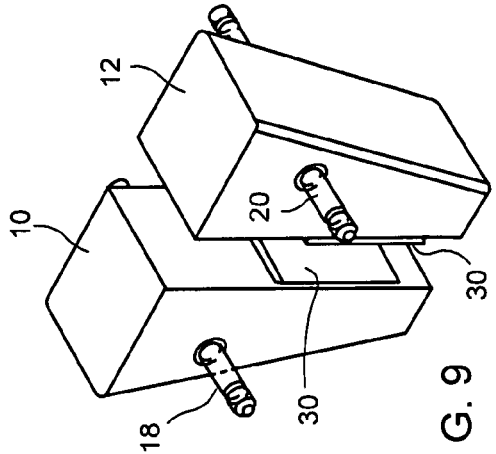
FIG. 8 is a perspective view of the jaws of the present invention, one with a swivel face which swivels with one degree of freedom about a vertical axis, another with a fixed gripping surface.

FIGS. 6 and 8 illustrate respective plan and perspective views of jaw 10 with a fixed gripping surface 24 facing jaw 12 with a swivel element 30 swiveling about a vertical axis as illustrated in FIG. 5.

Figure 7:
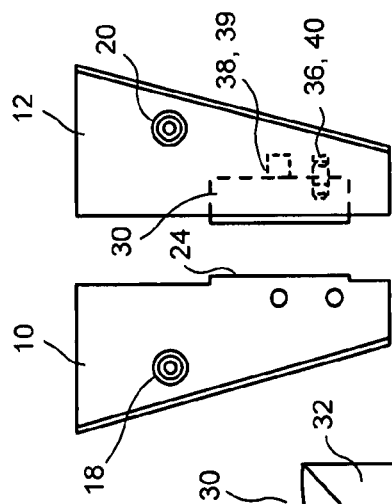
FIG. 7 is a plan view, partially in phantom, of the jaws of the present invention, each with a swivel face which swivel with one degree of freedom about a vertical axis.
Figure 9:
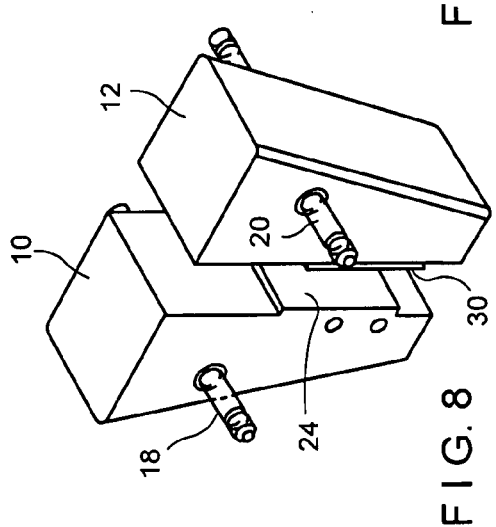
FIG. 9 is a perspective view of the jaws of the present invention, each with a swivel face which swivel with one degree of freedom about a vertical axis.

FIGS. 7 and 9 illustrate respective plan and perspective views of opposed jaws 10, 12, each with a swivel element 30 swiveling about a vertical axis as illustrated in FIG. 5.

Figure 10:
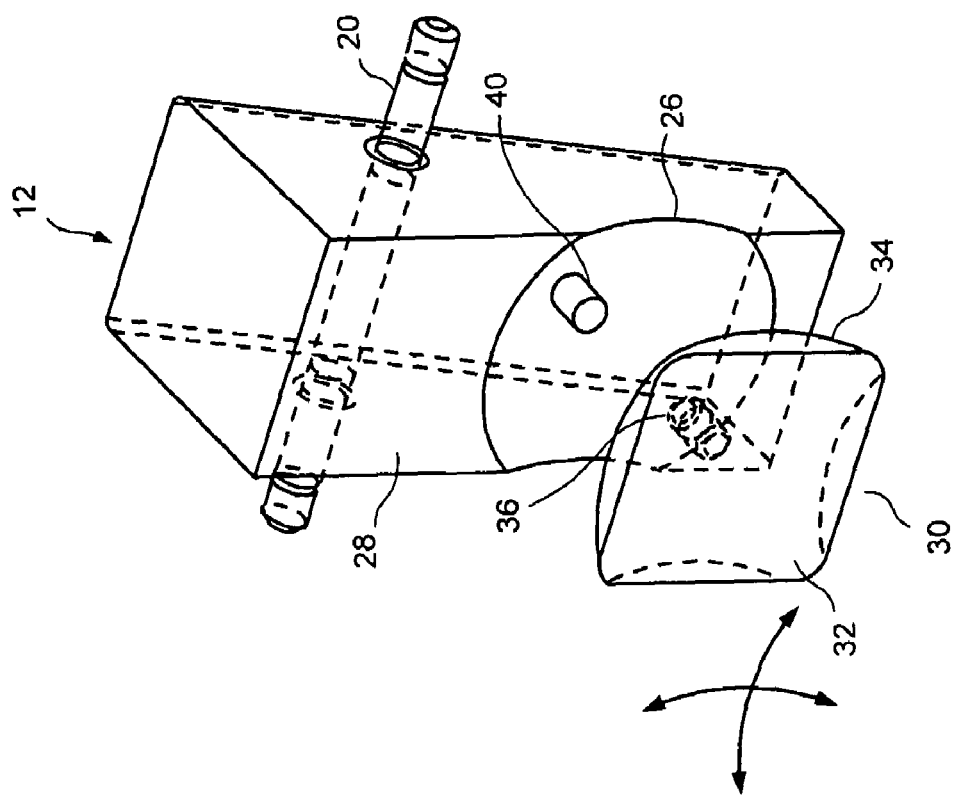
FIG. 10 is a partially exploded view of a single jaw of the present invention, shown with a swivel face which swivels with two degrees of freedom, with a partially spherical seat.

FIG. 10 shows a configuration wherein spherical concave seat 26 and rear spherical convex face 34 are formed from portions of spheres with a common geometric center thereby permitting swiveling (or spherical rotating) of swivel element 30, with a square gripping face 32, about two degrees of freedom (or two orthogonal axes).

Figure 11:
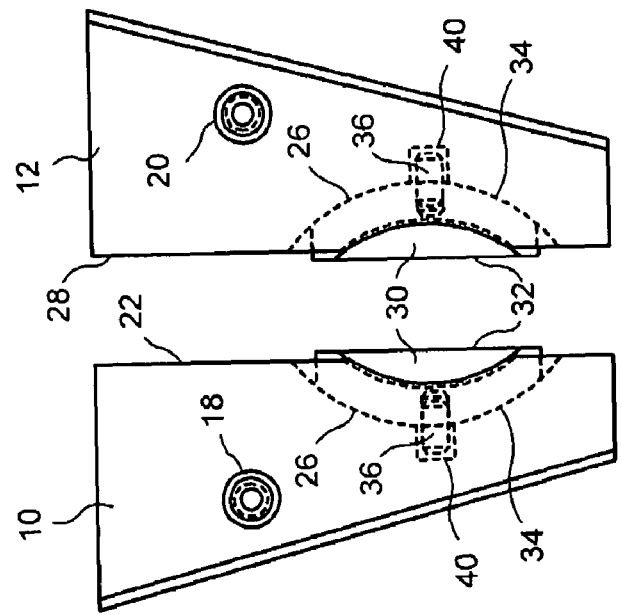
FIG. 11 is a plan view, partially in phantom, of two opposed jaws of the present invention, each with a swivel face which swivels about two degrees of freedom in a partially spherical seat.

FIGS. 11 and 13 illustrate respective plan and perspective views of opposed jaws 10, 12, each with a swivel element 30 swiveling with two degrees of freedom in a spherical seat 26 as illustrated in FIG. 10.

FIGS. 12 and 14 illustrate respective plan and perspective views of jaw 10 with a fixed gripping surface 24 facing jaw 12 which includes a swivel element 30 swiveling with two degrees of freedom in a spherical seat 26 as illustrated in FIG. 10.

In all cases, the swivel elements 30 swivel within the given degrees of freedom to accommodate the variations in the alignment of the surfaces of the sample being tested by tensile or similar tests. This swiveling occurs in response to opposed jaws 10, 12 being tightened around sample 1000.

It is envisioned that any of the variations of jaw 12 (swivel with a single degree of freedom about a horizontal axis, swivel with a single degree of freedom about a vertical axis, or swivel with two degrees of freedom about a point, the point being defined as the geometric center of the sphere of which the spherical seat is a portion) may face any of the variations of jaw 10 (fixed gripping surface, swivel with a single degree of freedom about a horizontal axis, swivel with a single degree of freedom about a vertical axis, or swivel with two degrees of freedom about a point). It is further envisioned that matching or differing gripping surfaces may be used, depending upon the characteristics of the sample, the desired tests, and the preferences of the testers.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. A head for securing a first of two opposing ends of a sample for material testing, including:
   a first jaw;
   a second jaw opposing the first jaw for engaging a first of two opposing ends of a sample therebetween;
   the first jaw including a first gripping face, wherein the first gripping face is fixed in orientation with respect to the first jaw;
   the second jaw includes a partially cylindrical seat and a swivel element swiveling about a single axis within the partially cylindrical seat, the swivel element further including a second gripping face opposing the first gripping face; and wherein said first and second gripping faces are parallel to a direction of force of the material testing.

2. The head of claim 1 wherein the swivel element includes a partially cylindrical wall for engaging within the partially cylindrical seat.

3. The head of claim 2 wherein the single axis is vertical with respect to downwardly pointing first and second jaws.

4. The head of claim 2 wherein the single axis is horizontal with respect to downwardly pointing first and second jaws.

5. The head of claim 2 wherein the swivel element is removable from the partially cylindrical seat.

6. A head for securing a first of two opposing ends of a sample for material testing, including:

a first jaw;

a second jaw opposing the first jaw for engaging a first of two opposing ends of the sample therebetween;

the first jaw includes a first partially cylindrical seat and a first swivel element swiveling about a single first axis within the first partially cylindrical seat;

the second jaw includes a second partially cylindrical seat and a second swivel element swiveling about a single second axis within the second partially cylindrical seat, the second swivel element further including a second gripping face opposing the first gripping face; and wherein said first and second gripping faces are parallel to a direction of force of the material testing.

7. The head of claim 6 wherein the first and second swivel elements include respective first and second partially cylindrical walls for engaging within the respective first and second partially cylindrical seat.

8. The head of claim 7 wherein the single first axis and the single second axis are vertical with respect to downwardly pointing first and second jaws.

9. The head of claim 7 wherein the single first axis and the single second axis are horizontal with respect to downwardly pointing first and second jaws.

10. The head of claim 7 wherein the single first axis is vertical with respect to downwardly pointing first and second jaws and the single second axis is horizontal with respect to downwardly pointing first and second jaws.

11. The head of claim 7 wherein the swivel element is removable from the partially cylindrical seat.

12. A head for securing a first of two opposing ends of a sample for material testing, including:

a first jaw;

a second jaw opposing the first jaw for engaging a first of two opposing ends of a sample therebetween;

the first jaw including a first gripping face, wherein the first gripping face is fixed in orientation with respect to the first jaw;

the second jaw includes a partially spherical seat and a swivel element swiveling with two degrees of freedom within the partially spherical seat, the swivel element further including a second gripping face opposing the first gripping face; and wherein said first and second gripping faces are parallel to a direction of force of the material testing.

13. The head of claim 12 wherein the swivel element includes a partially spherical wall for engaging within the partially spherical seat.

14. The head of claim 12 wherein the swivel element swivels with two degrees of freedom about a point defined by the partially spherical seat.

15. The head of claim 12 wherein the swivel element is removable from the partially spherical seat.

16. A head for securing a first of two opposing ends of a sample for material testing, including:

a first jaw;

a second jaw opposing the first jaw for engaging a first of two opposing ends of a sample therebetween;

the first jaw includes a first partially spherical seat and a first swivel element swiveling with two degrees of freedom within the first partially spherical seat;

the second jaw includes a second partially spherical seat and a second swivel element swiveling with two degrees of freedom within the second partially spherical seat, the second swivel element further including a second gripping face opposing the first gripping face; and wherein said first and second gripping faces are parallel to a direction of force of the material testing.

17. The head of claim 16 wherein the first and second swivel elements includes a respective first and second partially spherical wall for engaging within the respective first and second partially spherical seats.

18. The head of claim 16 wherein the first swivel element swivels with two degrees of freedom about a point defined by the first partially spherical seat.

19. The head of claim 18 wherein the second swivel element swivels with two degrees of freedom about a point defined by the second partially spherical seat.

20. The head of claim 16 wherein the first and second swivel elements are removable from the respective first and second partially spherical seats.

* * * * *